United States Patent
Wu et al.

(10) Patent No.: US 9,996,739 B2
(45) Date of Patent: Jun. 12, 2018

(54) SYSTEM AND METHOD FOR AUTOMATIC GAIT CYCLE SEGMENTATION

(71) Applicant: Conduent Business Services, LLC, Dallas, TX (US)

(72) Inventors: Hao Wu, Pittsford, NY (US); Beilei Xu, Penfield, NY (US); Wencheng Wu, Webster, NY (US); Robert P. Loce, Webster, NY (US)

(73) Assignee: Conduent Business Services, LLC, Dallas, TX (US)

( * ) Notice: Subject to any disclaimer, the term of this patent is extended or adjusted under 35 U.S.C. 154(b) by 0 days. days.

(21) Appl. No.: 15/283,663

(22) Filed: Oct. 3, 2016

(65) Prior Publication Data

US 2017/0243057 A1 Aug. 24, 2017

Related U.S. Application Data

(60) Provisional application No. 62/297,341, filed on Feb. 19, 2016.

(51) Int. Cl.
G06K 9/00 (2006.01)
G06T 7/00 (2017.01)
G06T 7/20 (2017.01)

(52) U.S. Cl.
CPC ..... *G06K 9/00348* (2013.01); *G06K 9/00885* (2013.01); *G06T 7/0097* (2013.01); *G06T 7/20* (2013.01); *G06T 2207/30196* (2013.01)

(58) Field of Classification Search
CPC ........... G06K 9/00288; G06K 9/00885; G06K 9/00892; G06K 9/6293

USPC ....... 382/115, 128, 170, 209, 278, 282, 291; 340/5.81, 5.82, 5.83
See application file for complete search history.

(56) References Cited

U.S. PATENT DOCUMENTS

| | | | |
|---|---|---|---|
| 7,227,893 B1 * | 6/2007 | Srinivasa | G06K 9/00771 348/155 |
| 7,330,566 B2 | 2/2008 | Cutler | |
| 7,421,369 B2 * | 9/2008 | Clarkson | A61B 5/061 482/1 |

(Continued)

FOREIGN PATENT DOCUMENTS

JP 2010017447 1/2010

OTHER PUBLICATIONS

Johansson, Gunnar, "Visual perception of biological motion and a model for its analysis", Perception & Psychophysics, 1973, vol. 14, No. 2, 201-211.

(Continued)

*Primary Examiner* — Yosef Kassa
(74) *Attorney, Agent, or Firm* — Fay Sharpe LLP

(57) ABSTRACT

A computer-implemented system and method for gait analysis of a subject. The method includes obtaining visual data from an image capture device positioned in front of or behind the subject, the plurality of image frames capturing at least one gait cycle of the gait of the subject, detecting one or more prescribed features within the plurality of image frames, analyzing each of the plurality of image frames to detect cross-frame stability of the one or more prescribed features, and segmenting the gait of the subject into at least one gait cycle based at least in part on the detected cross-frame stability of the one or more prescribed features.

19 Claims, 8 Drawing Sheets

(56) References Cited

U.S. PATENT DOCUMENTS

| | | | |
|---|---|---|---|
| 7,660,439 B1* | 2/2010 | Lu | G06K 9/00711 348/699 |
| 7,804,998 B2 | 9/2010 | Mundermann | |
| 7,878,990 B2* | 2/2011 | Al-Obaidi | A61B 5/6829 600/592 |
| 8,073,521 B2 | 12/2011 | Liew | |
| 8,154,644 B2* | 4/2012 | Thorn | G06F 3/011 348/333.02 |
| 8,206,325 B1* | 6/2012 | Najafi | A61B 5/1116 600/587 |
| 8,246,354 B2 | 8/2012 | Chu | |
| 8,280,678 B2* | 10/2012 | Lee | G01C 22/006 701/527 |
| 8,300,890 B1* | 10/2012 | Gaikwad | G06K 9/00771 382/103 |
| 8,373,753 B2* | 2/2013 | Cheng | G06K 9/00771 348/143 |
| 8,409,292 B2* | 4/2013 | Michelson | A61F 2/30771 606/246 |
| 8,447,272 B2* | 5/2013 | Faith | G06Q 30/0201 455/410 |
| 8,514,236 B2* | 8/2013 | Kobla | A61B 5/1113 345/547 |
| 8,854,182 B2 | 10/2014 | Lobean | |
| 2004/0228503 A1 | 11/2004 | Cutler | |
| 2014/0261887 A1 | 9/2014 | Groot | |
| 2014/0358040 A1 | 12/2014 | Kim | |
| 2015/0173652 A1 | 6/2015 | Brunner | |
| 2015/0196231 A1 | 7/2015 | Ziaie | |
| 2017/0243057 A1 | 8/2017 | Wu | |
| 2017/0243354 A1 | 8/2017 | Tafazzoli | |

OTHER PUBLICATIONS

Mouta, Sandra, Santos, Jorge, Rybarczyk, Yves, "Visual perception of biological motion direction and velocity: global and local factors", Dept. of Psychology, I.E.P., University of Minho.

Nixon, Mark S., Carter, John N., "Advances in Automatic Gait Recognition", School of Electronics and Computer Science, University of Southampton.

Wang, Jin, She, Mary, Nahavandi, Saeid, "A Review of Vision-based Gait Recognition Methods for Human Identification", 2010 Digital Image Computing: Techniques and Applications, pp. 320-327.

Benabdelkader, Chiraz, Cutler, Ross; David, Larry, "Stride and Cadence as a Biometric in Automatic Person Identification and Verification", Automatic Face and Gesture Recognition, 2002. Proceedings. Fifth IEEE International Conference on IEEE, 2002.

Bouchrika, Imed, "Evidence Evaluation of Gait Biometrics for Forensic Investigation", Multimedia Forensics and Security. Springer International Publishing, 2017. 307-326.

Martin-Félez, Raúl; MollinedaJavier, Ramón A., Sánchez, Salvador, "Human Recognition Based on Gait Poses (Pattern Recognition and Image Analysis)", Iberian Conference on Pattern Recognition and Image Analysis IbPRIA 2011: Pattern Recognition and Image Analysis pp. 347-354.

Hoeger, Werner W.K., Bond, Laura, Ransdell, Lynda, Shimon, Jane M., Merugu, Sunitha, "One-Mile Step Count at Walking nad Running Speeds", ACSM's Health & Fitness Journal vol. 12, No. 1 (2008), pp. 14-19.

Stone, Erik E., Skubic, Marjorie, "Capturing Habitual, In-Home Gait Parameter Trends Using an Inexpensive Depth Camera", 34th Annual International Conference of IEEE EMBS, Aug. 28-Sep. 1, 2012, pp. 5106-5109.

Sisto, Sue Ann, "An Overview of the Value of Information Resulting from Instrumented Gait Analysis for the Physical Therapist", RRDS Gait Analysis in the Science of Rehabilitation.

Park, Kiwon, Dissertation: "Quantitative Assessment of Human Gait Patterns Using Biomechanical and Dynamical Tools", University of Illinois, 2012.

Tafazzoli, F, Xu, B., Wu, W., Loce, R., "Automatic Frontal-View Gait Segmentation for Abnormal Gait Quantification,", U.S. Appl. No. 15/283,603, filed Oct. 3, 2016.

Mark S. Nixon, Tieniu Tan, Rama Chellappa, Human Identification Based on Gait, Springer, 2006, Title page and p. 1, https://books.google.com/books?id=tD42mXCGRGcC&pg=PR4&lpg=PR4&dq=Mark+S.+Nixon,+Tieniu+Tan,+Rama+Chellappa,+%E2%80%9CHuman+Identification+Based+on+Gait%E2%80%9D&source=bl&ots=YDiW8WA2Fx&sig=KoL7rtlochXooEhh-BZM8ulU8C6w&hl=en&sa=X&ved=0ahUKEwH47_mzNfVAh-XCgFQKHXNmD-UQ6AEIUDAJ#v=onepage&q=Mark%20S.%20Nixon%2C%20Tieniue%20Tan%2C%20Rama%.

Felzenszwalb, Pedro F., Girshick, Ross B., McAllester, David, Ramanan, Deva, "Object Detection with Discriminatively Trained Part-Based Models", IEEE Transactions on Pattern Analysis and Machine Intelligence, vol. 32, No. 9, Sep. 2010.

Tomasi, Carlo, Kanade, Takeo, "Detection and Tracking of Point Features", Computer Science Department, Carnegie Mellon university, Apr. 1991.

Xu, Xin, Tang, Jinshan, Zhang, Xiaolong, Liu, Xiaoming, Zhang, Hong, Qiu Yimin, "Exploring Techniques for Vision Based Human Activity Recognitino: Methods, Systems, and Evaluation", Sensors 2013, 13, 1635-1650.

Park, Dennis, Ramanan, Deva, "N-best maximal decoders for part models", International Conference on Computer Vision (ICCV) Barcelona, Spain, pp. 2627-2634, Nov. 2011.

Wang, Heng, Klaser, Alexander, Schmid, Cordelia, Cheng-Lin, Liu, "Action Recognition by Dense Trajectories", CVPR 2011—IEEE Conference on Computer Vision & Pattern Recognition, Jun. 2011, pp. 3169-3176.

Hamdoun, Omar, Moutarde, Fabien, Stanciulescu, Bogdan, Steux Bruno, "Person re-identification in multi-camera system by signature based on interest point descriptors collected on short video sequences", 2nd ACM/IEEE International Conference on Distributed Smart Cameras (ICDSC-08), Sep. 2008, Stanford, Palo Alto, US.

Yang, Yi, Ramanan, Deva, "Articulated Human Detection with Flexible Mixtures-of-Parts", IEEE Transactions on Pattern Analysis and Machine Intelligence (PAMI), vol. 61, No. 1, pp. 55-79, 2013.

Zhou, Xiaowei, Leonardos, Spyridon, Hu, Xiaoyan, Daniilidis, Kostas, "3D Shape Estimation from 2D Landmarks: A Convex Relaxation Approach", IEEE Conference on Computer Vision and Pattern Recognition (CVPR), pp. 259-267, 2015.

MoCap: Carnegie Mellon University Motion Capture database. http://mocap.cs.cmu.edu/.

\* cited by examiner

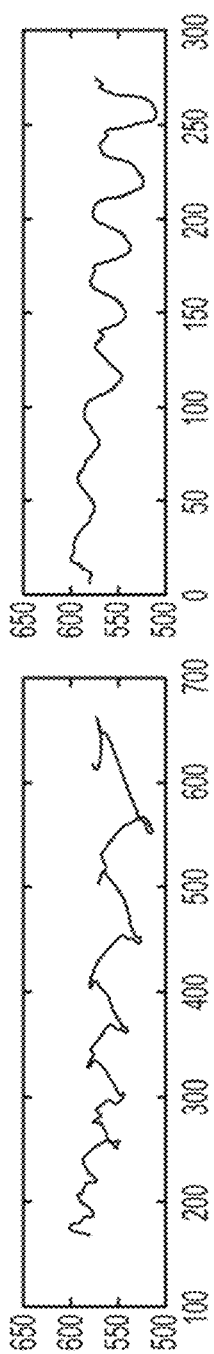

SYSTEM AND METHOD FOR AUTOMATIC GAIT CYCLE SEGMENTATION

CROSS REFERENCE TO RELATED PATENTS AND APPLICATIONS

This application claims priority to and the benefit of the filing date of U.S. Provisional Patent Application Ser. No. 62/297,341, filed Feb. 19, 2016, which application is hereby incorporated by reference.

BACKGROUND

Human gait, a biometric aimed to recognize individuals by the way they walk, has recently come to play an increasingly important role in different applications such as access control and visual surveillance. Although no two body movements are ever the same, gait is as characteristic of an individual analogous to other biometrics. Psychological, medical, and biomechanical studies support the notion that humans effortlessly recognize people by the way they walk and basic gait patterns are unique to each individual. In contrast to many established biometric modalities such as face, fingerprint or retina, gait can be analyzed from a distance and can be observed without notification to the subject or compliance by the subject. In fact, the considerable attention towards this biometric has been due to its ability to ascertain somebody's identity at a distance while being noninvasive and non-perceivable.

However, human gait analysis and assessment involves challenging issues due to the highly flexible structure and self-occlusion of the human body. These issues mandate using complicated processes for the measurement and analysis of gait in marker-less video sequences. For instance, footwear, physical conditions such as pregnancy, leg or foot injuries, or even drunkenness can change the manner of walking. Like most biometrics, gait will inherently change with age. Therefore, gait can disclose more than identity.

Human gait constitutes an essential metric related to a person's health and well-being. Degradation of a person's walking pattern decreases quality of life for the individual and may result in falls and injuries. In one estimate, 1 out of every 3 elder adults (over the age of 65) falls each year. And these related injuries cost $20 billion per year in the United States. There are different types of physiological and anatomical factors that can adversely affect gait, such as neurological maladies (e.g., Parkinson's disease or multiple sclerosis), degradation of the bones, joints or muscles, lower limb injury or pains and geriatric diseases, such as osteoporosis, which affect a large percentage of the population. The common symptoms for these cases include moving with slow pace, unstable standing, tilted walking, mini-step walking, altering velocity, length of the stride and cadence. Therefore, passive monitoring of a person's gait and the detection of deviations from normal patterns can support current frailty assessments leading to an improved and earlier detection of many diseases, or provide valuable information for rehabilitation. On the other hand, assessment is important for recuperative efforts.

The traditional scales used to analyze gait parameters in clinical conditions are semi-subjective, carried out by specialists who observe the quality of a patient's gait by making him/her walk. This is sometimes followed by a survey in which the patient is asked to give a subjective evaluation of the quality of his/her gait. The disadvantage of these methods is that they give subjective measurements, particularly concerning accuracy and precision, which have a negative effect on the diagnosis, follow-up and treatment of the pathologies.

Wearable sensors are being developed to add objectivity and move the assessment into a passive (e.g., home) setting, rather than costly, infrequent clinical assessments. The various wearable sensor-based systems that have been proposed use sensors located on several parts of the body, such as feet, knees, thighs or waist. Different types of sensors are used to capture the various signals to characterize the human gait. However, their major disadvantage is the need to place devices on the subject's body, which may be uncomfortable or intrusive. Also, the use of wearable sensors allows analysis of only a limited number of gait parameters. Besides, the analysis of the signals is computationally complex and presents the problem of excessive noise.

The relationship between stride length and frequency is of fundamental concern to many studies of walking. Other than wearable or ground sensors, cameras are also used to analyze gait. Prior camera-based approaches have included the following:

Marker based: this method requires the subject wear easily detectable markers on the body, usually at joint locations. The 2D or 3D locations of the markers will be extracted in a monocular or multi-camera system. The marker locations or the relationships between them are then used to segment each stride/step.

Marker-less: this category of methods can be divided into two sub-categories: holistic (usually model free) and model based. For holistic methods, human subjects are usually first detected, tracked and segmented; then gait is usually characterized by the statistics of the spatiotemporal patterns generated by the silhouette of the walking person. A set of features/gait signatures is then computed from the patterns for segmentation/recognition, etc. One approach analyzed the auto correlation signals of the image sequence. Another approach used XT & YT slices for gait analysis. Model-based methods apply human body/shape or motion models to recover features of gait mechanics and kinematics. The relationship between body parts will be used to segment each stride/step or for other purposes. Models include generative and discriminative models.

For most gait analysis methods, segmenting gait cycle precisely is one of the most important steps and building blocks. Stride-to-stride measurement of gait signals is essential for disease diagnosing and monitoring, such as Parkinson's. As such diseases usually progress over a long period of time, it is very desirable to enable frequent and objective assessments to continuously understand such patients' ambulatory condition. Gait signals can come from wearable devices or camera data. Current methods for gait analysis include manual or automatic segmentation based on some gait signals such as feet distance or knee angles, etc. Visual inspection of gait from real-time actions or video recordings is subjective and requires a costly trained professional to be present, thereby limiting the frequency at which evaluations can be performed. Wearables capture only a portion of gait signal (depending on where the sensors are positioned) and require compliance of a patient to consistently wear the device if day-to-day measurement is to be taken. Current computer vision techniques can be categorized into marker-based and marker-less approaches. Similar to wearables, marker-based technologies require precise positioning of markers on subjects, which is not feasible for day-to-day monitoring. Monocular marker-less technologies often require identifying human body parts first, which is very challenging due to variations in viewing angle and appearance. Hence, the current monocular marker-less method is usually performed in clinical settings where the viewing angle and camera-to-subject distance are fixed, and the method may not be robust enough in an assisted living or traditional home setting.

It is believed that most vision based methods explore the spatial change of a feature (could be joint location, body part location, or holistic image features, etc.) or the relationship between them (distance between two feet, knee angles, etc.). These methods require accurate detections of body parts or landmarks, which are usually highly view-dependent and very challenging and thus less robust in practice.

INCORPORATION BY REFERENCE

The following references, the disclosures of which are incorporated by reference herein in their entireties, and filed concurrently, are mentioned:

U.S. application Ser. No. 15/283,603, filed Oct. 3, 2016, by Tafazzoli et al., entitled "AUTOMATIC FRONTAL-VIEW GAIT SEGMENTATION FOR ABNORMAL GAIT QUANTIFICATION"; and, U.S. application Ser. No. 15/283,629, filed Oct. 3, 2016, by Xu et al., entitled "COMPUTER VISION SYSTEM FOR AMBIENT LONG-TERM GAIT ASSESSMENT".

The following reference, the disclosure of which is incorporated by reference herein in its entirety, is mentioned:

U.S. application Ser. No. 14/963,602, filed Dec. 9, 2015, by Bernal, et al., entitled "COMPUTER-VISION-BASED GROUP IDENTIFICATION)".

BRIEF DESCRIPTION

According to one aspect a computer-implemented method for gait analysis of a subject comprises obtaining visual data from an image capture device, the visual data comprising a plurality of image frames of the subject over a period of time walking, the plurality of image frames capturing at least one gait cycle of the gait of the subject, detecting one or more prescribed features within the plurality of image frames, analyzing each of the plurality of image frames to detect cross-frame stability of the one or more prescribed features, and segmenting the gait of the subject into at least one gait cycle based at least in part on the detected cross-frame stability of the one or more prescribed features.

The one or more prescribed features can include edge/contour/silhouette pixels, Harris corners, dense SIFT/SURF features, color features or other local/regional image features. The method can further comprise detecting a plurality of spatiotemporal clusters of edge pixels, the spatiotemporal clusters corresponding to temporarily stable features in the plurality of image frames, and/or analyzing the plurality of spatiotemporal clusters to segment the gait. The temporarily stable features can include features detected to be stationary in more than two image frames and less than an upper limit of image frames, such as, for example, 13 image frames. The method can also include analyzing the gait segment for at least one of a stride duration, cadence, stride length or base gait. The obtaining visual data from an image capture device can include using a camera mounted in an elongate hallway in which the subject can walk towards and away from the camera.

In accordance with another aspect, a system for gait analysis of a subject comprises an image capture device operatively coupled to a data processing device, the image capture device configured to capture visual data comprising a plurality of image frames of the subject walking, the plurality of image frames capturing at least one gait cycle of the gait of the subject, a processor-usable medium embodying computer code, said processor-usable medium being coupled to said data processing device, said computer code comprising instructions executable by said data processing device and configured for: detecting one or more prescribed features within the plurality of image frames, analyzing each of the plurality of image frames to detect cross-frame stability of the one or more prescribed features, and segmenting the gait of the subject into at least one gait cycle based at least in part on the detected cross-frame stability of the one or more prescribed features.

The one or more prescribed features can include edge/contour/silhouette pixels, Harris corners, dense SIFT/SURF features, color features or other local/regional image features. The data processing device can be further configured for detecting a plurality of spatiotemporal clusters of edge pixels, the spatiotemporal clusters corresponding to temporarily stable features in the plurality of image frames. The data processing device can be further configured for analyzing the plurality of spatiotemporal clusters to segment the gait. The temporarily stable features can include features detected to be stationary in more than two image frames and less than 13 image frames. The data processing device can be further configured for analyzing the gait segment for at least one of a stride duration, cadence, stride length or gait base. The obtaining visual data from an image capture device can include using a camera mounted in an elongate hallway in which the subject can walk towards and away from the camera.

In accordance with another aspect, a non-transitory computer-usable medium for gait analysis of a subject, said computer-usable medium embodying a computer program code, said computer program code comprising computer executable instructions configured for: obtaining visual data from an image capture device, the visual data comprising a plurality of image frames of the subject over a period of time walking, the plurality of image frames capturing at least one gait cycle of the gait of the subject, detecting one or more prescribed features within the plurality of image frames, analyzing each of the plurality of image frames to detect cross-frame stability of the one or more prescribed features; and segmenting the gait of the subject into at least one gait cycle based at least in part on the detected cross-frame stability of the one or more prescribed features.

The one or more prescribed features can includes include edge/contour/silhouette pixels, Harris corners, dense SIFT/SURF features, color features or other local/regional image features. The computer executable instructions can be further configured for detecting a plurality of spatiotemporal clusters of edge pixels, the spatiotemporal clusters corresponding to temporarily stable features in the plurality of image frames. The computer executable instructions can be further configured for analyzing the plurality of spatiotemporal clusters to segment the gait. The temporarily stable features can be features detected to be stationary in more than two image frames and less than 13 image frames. The computer executable instructions can be further configured for analyzing the gait segment for at least one of a stride duration, cadence, stride length or gait base, and wherein the obtaining visual data from an image capture device includes using a camera mounted in an elongate hallway in which the subject can walk towards and away from the camera.

BRIEF DESCRIPTION OF THE DRAWINGS

FIG. 9(a) shows the XY view of the centers of $F_{stable}(x, y;t)$; and

FIG. 9(b) shows the XT view of the centers of $F_{stable}(x, y;t)$.

DETAILED DESCRIPTION

Figure 1:
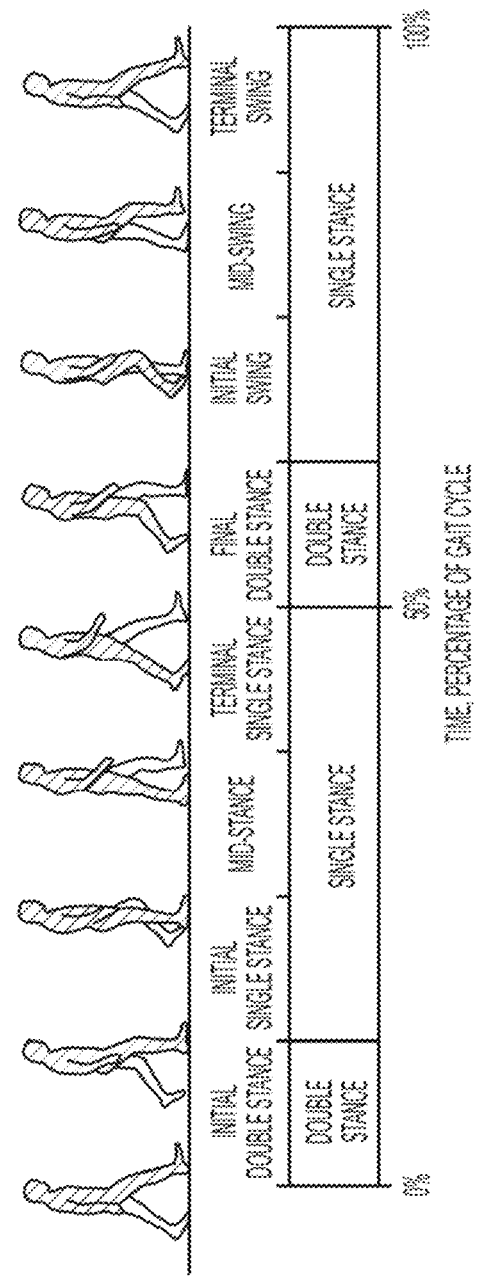
FIG. 1 is a graphical depiction of various exemplary segments of a gait cycle.

The present disclosure sets forth a system and method that utilizes the temporal duration of features, which is based on the observation that during the single stance phase of a walking cycle, there is one foot/part of the leg that is not moving as shown in FIG. 1. The method does not require body part detection/segmentation and is view independent. The method is more accurate, robust and computationally efficient compared to methods relying on spatial changes/relationships of features.

In addition, aspects of the present disclosure can achieve an objective evaluation of different gait parameters, by applying Computer Vision techniques using an existing monitoring system without substantial additional cost or equipment, and can perform assessment during a user's daily activity without the requirement to wear a device or special clothing (e.g., uniform with distinct marks on certain joints of the person). Computer vision approaches can allow simultaneous, in-depth analysis of a higher number of parameters than current wearable systems. Unlike wearable sensors, computer vision approaches are not restricted by power consumption. The algorithms set forth herein can provide a consistent, objective measure, which reduces error and variability incurred by subjective techniques. To achieve these goals, a body and gait representation is generated that can provide gait characteristics of an individual, while applying generally to classification and quantification of gait across individuals.

Figure 2:
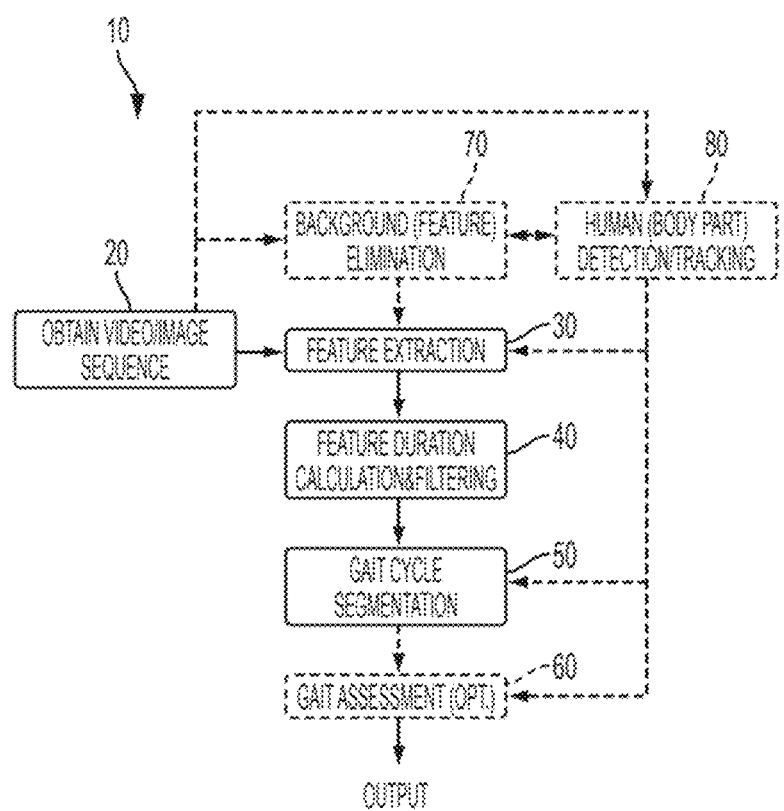
FIG. 2 is a flowchart of a method in accordance with the present disclosure.

A fast, robust and accurate gait cycle segmentation system and method is set forth, which can use a single non-calibrated camera and is not limited by viewing angles. With reference to FIG. 2, the method 10 includes one or more of the following steps: 1) acquisition of a sequence of images or video frames of interest (step 20); 2) feature detection in each frame (step 30); 3) cross-frame feature stability/duration calculation and filtering (step 40); 4) gait cycle/step segmentation (step 50); 5) (optional) gait assessment (step 60). Optional steps include background elimination (step 70) and human body part detection/tracking (step 80). All of these steps will be described in detail below.

After gait cycle/step segmentation, stride-to-stride duration and length can be calculated to assist gait quantification/assessment. Further extraction of other gait characteristics can also be performed based on the cycle segmentation results. The system and method have been tested on videos from different viewing angles. The overall system can also comprise suitable image/video acquisition, processing, transmission and data storage devices.

Figure 3:
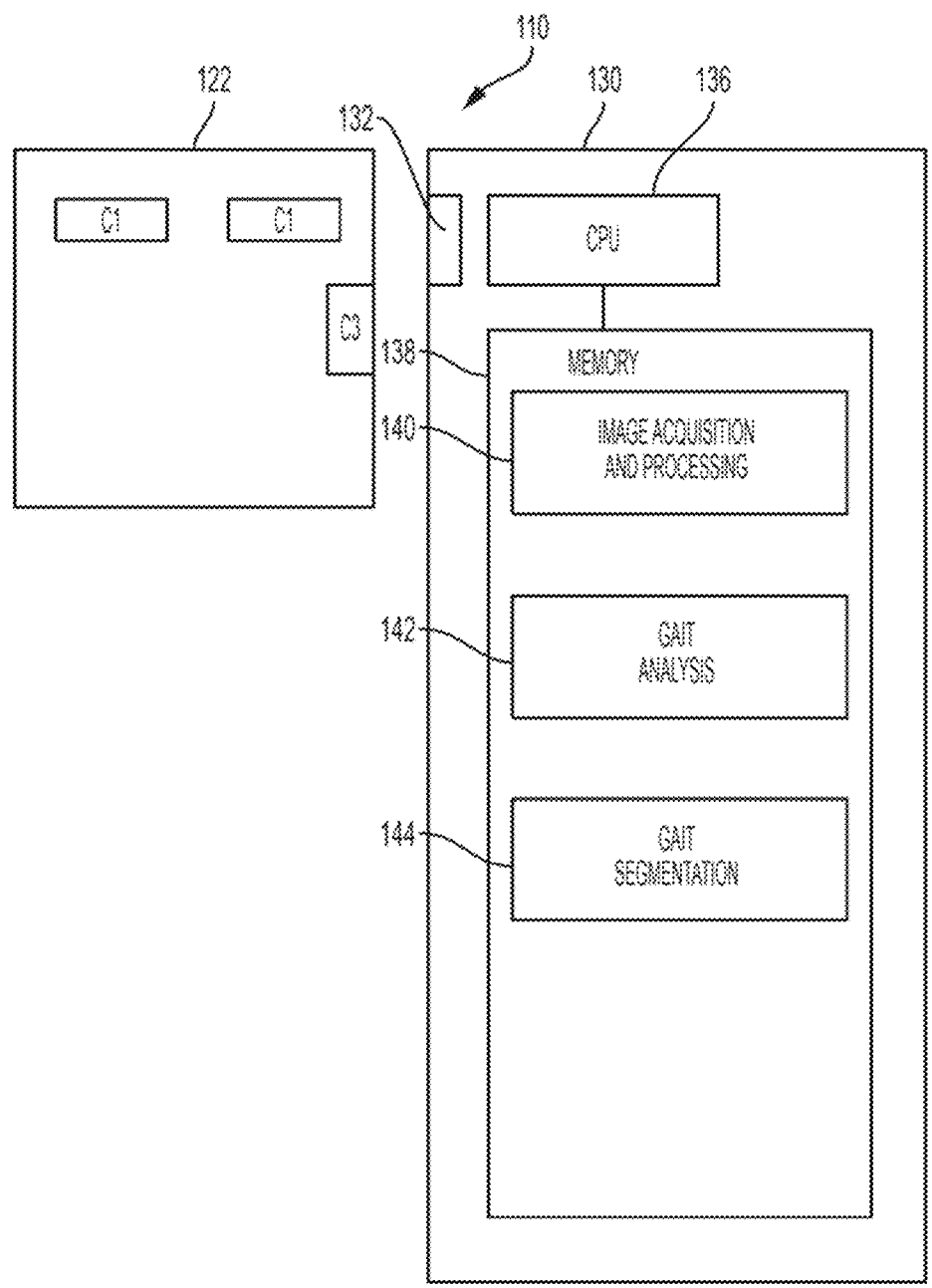
FIG. 3 is a schematic block diagram of an exemplary system in accordance with the present disclosure.

In FIG. 3, an exemplary system 110 in accordance with the present disclosure is illustrated in block diagram form in connection with a patient space 122 such as a hallway, waiting room, or the like. It will be appreciated that patient space 122 is exemplary, and that the system 110 can be implemented in virtually any location or setting (e.g., public or private spaces, etc.) provided suitable images of a subject passing by, approaching and/or departing can be obtained. In the exemplary embodiment, a plurality of cameras C1, C2 and C3 are positioned at different locations within the patient space 122. However, any number of cameras can be utilized.

The cameras C1, C2 and C3 are connected to a computer 130 and supply visual data comprising one or more image frames thereto via a communication interface 132. It will be appreciated that the computer 130 can be a standalone unit configured specifically to perform the tasks associated with the aspects of this disclosure. In other embodiments, aspects of the disclosure can be integrated into existing systems, computers, etc. The communication interface 132 can be a wireless or wired communication interface depending on the application. The computer 130 further includes a central processing unit 136 coupled with a memory 138. Stored in the memory 138 are various modules including an image acquisition module 140, a gait analysis module 142, and a gait segmentation module 144. Visual data received from the cameras C1, C2 and C3 can be stored in memory 138 for processing by the CPU 136 in accordance with this disclosure. It will further be appreciated that the various modules can be configured to carry out the functions described in detail in the following paragraphs.

Returning now to a discussion of the method/process, in step 20, acquiring or identifying a suitable sequence for the following gait analysis is desired because gait analysis can only be performed when a human subject is walking. Both manual and automatic methods can be used to perform this step. In one embodiment, automatic approaches can include human walking activity recognition/detection, human tracking and trajectory-based analysis, etc.

In step 30, an image feature detection method can be performed on each frame of the acquired suitable images or video frames. The image features here can be any type of computer vision features, such as edge/contour/silhouette pixels, Harris corners, dense SIFT/SURF features, color features or other local/regional image features. It can also be a combination of different types of features to improve robustness. Any approaches to identify background regions can also be employed to eliminate unwanted features not related to human walking (e.g., at step 70). To identify the regions, background subtraction methods can be applied, including methods such as parametric and non-parametric methods, or frame difference. Performing human body detection or body part identification prior to the feature extraction can also aid in eliminating unwanted regions/features (e.g., at step 80).

Figure 4C:
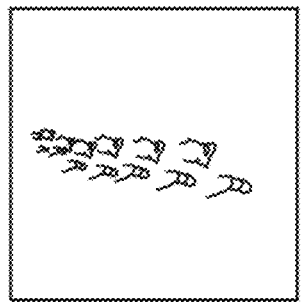
FIG. 4(c) shows the accumulated edge pixels in gray scale (high intensity means higher reoccurrence rate/longer duration) when using only the lower half of the bounding box shown in FIG. 4(a)
Figure 4B:
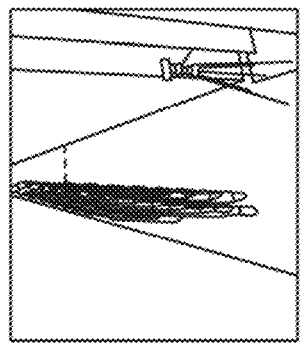
FIG. 4(b) shows the accumulated edge pixels across time when entire frame was used.
Figure 4A:
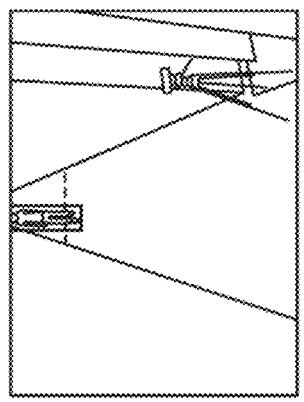
FIG. 4(a) shows detected edge pixels at one example frame, when given the bounding box of the human subject.

In one embodiment, edge/contour/silhouette pixels are detected as the features to be analyzed in each image or video frame and the bounding box of the human subject is used as the region of interest (ROI) for feature detection. FIG. 4(a) shows the detected edge pixels at one example frame, when given the bounding box of the human subject, edge detection was performed only within the box. FIG. 4(b) shows the accumulated edge pixels across time when entire frame was used. The colors reflect the duration/reoccurrence of the edge pixels: yellow indicates high reoccurrence rate/longer duration and blue indicates lower reoccurrence rate/duration. If no background subtraction or human (body) detection is performed before feature detection, the duration/reoccurrence rate difference between the background and human subject can also be used to eliminate background/unwanted features. FIG. 4(c) shows the accumulated edge pixels in gray scale (high intensity means higher reoccurrence rate/longer duration) when using only the lower half of the bounding box as the ROI. Any other pre-processing to enhance the feature detection performance can also be used, such as smoothing or/and contrast enhancement, etc. In one embodiment, low pass filtering was used to reduce noise to smooth the image/frame before performing edge detection.

Since background features can also be easily removed in the next steps when evaluating the duration/reoccurrence rate of features, performing background (feature) elimination before feature detection is only optional, so is the human detection/body part identification step.

After detecting the features, evaluating the feature stability/duration is next at step 40. For a static camera system, the background features usually have very long durations/good stability across time while the moving parts of the human body are generally unstable or have short durations/poor stability. The features from the supporting foot/leg during each single stance phase have more duration/stability. The single-stance phase of a normal walking human usually lasts about 0.4 seconds on average. This means that for a normal 30 frame/s video, there will be approximately 12 frames during a single-stance phase. Since during the double stance, both feet/legs have unmoved/stable parts, when counting for the longest duration of the features from the supporting foot/leg, it is about the duration of one step, which is a little longer than the duration of a single stance phase (on average 0.5 s).

Figure 5A:
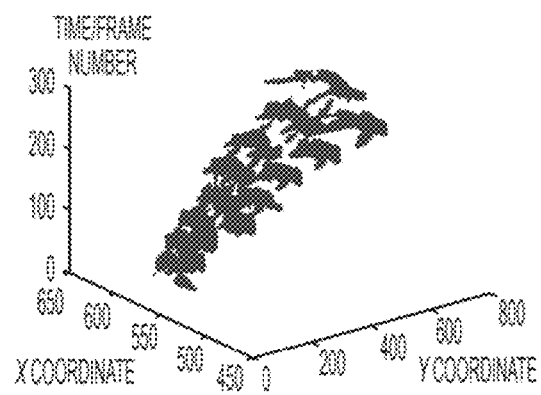
FIG. 5(a) is a graph showing the 3D (x-y-t) map of detected temporarily stable features, which are the stable edge pixels in the exemplary embodiment.
Figure 5B:
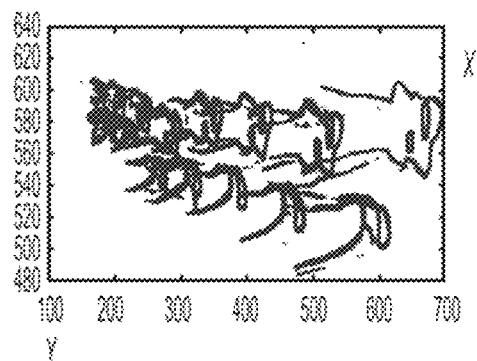
FIG. 5(b) is a graph showing the x-y projection of detected temporarily stable features of FIG. 5(a)
Figure 5C:
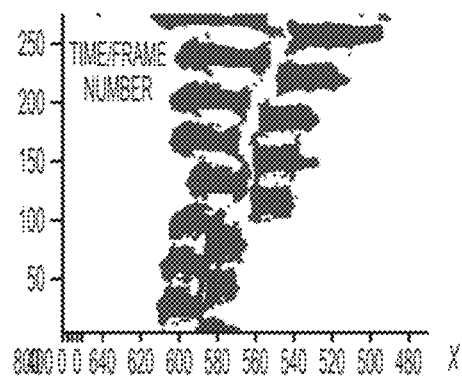
FIG. 5(c) is a graph showing the x-t projection of detected temporarily stable features of FIG. 5(a)

FIG. 5(a) shows the 3D (x-y-t) map of detected temporarily stable features, which are the stable edge pixels in the exemplary embodiment. FIGS. 5(b) and 5(c) show the x-y and x-t projections respectively, where x and y refer to the horizontal and vertical directions in each frame. The threshold of duration for temporarily stable feature detection can be based on a rule of thumb or experimental results or a calculated optimal value. Duration longer than 4 frames is used in FIGS. 5(a)-5(c). A longer duration threshold generally results in fewer detected features.

Figure 6:
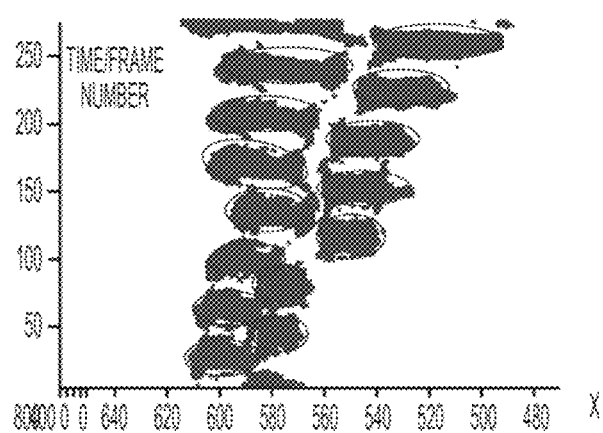
FIG. 6 illustrates the detected spatiotemporal clusters from the possible detected spatiotemporal clusters using FIG. 5(c) data.

Gait cycle segmentation occurs at step 50. The exemplary embodiment uses clustering methods to find the 3D or 2D spatiotemporal clusters created by the temporarily stable features. FIG. 6 illustrates the detected spatiotemporal clusters from the possible detected spatiotemporal clusters using FIG. 5(c) data. As will be appreciated, gait cycles, stride or step duration can be calculated from the detected clusters with further investigation.

Figure 7:
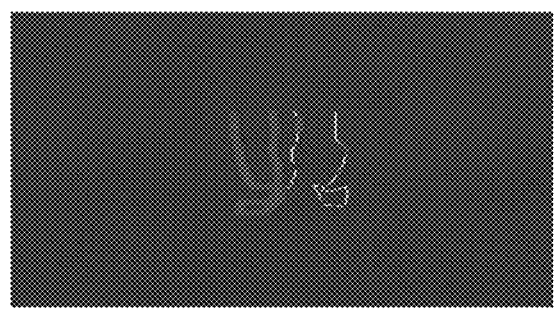
FIG. 7 illustrates all detected features at a time (edge pixels in the exemplary embodiment) and the green highlighted pixels are the detected temporarily stable edge pixels at that time.
Figure 8A:
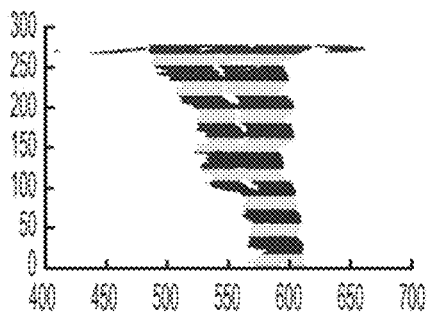
FIG. 8(a) shows the x-t view of each detected step.
Figure 8B:
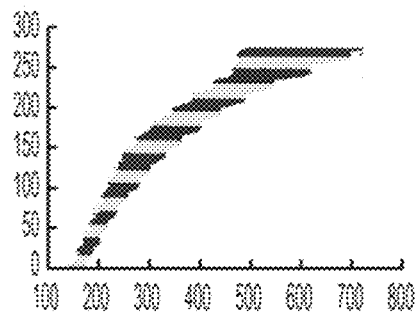
FIG. 8(b) shows the y-t view of each detected step when a human walks through a hallway.
Figure 8C:
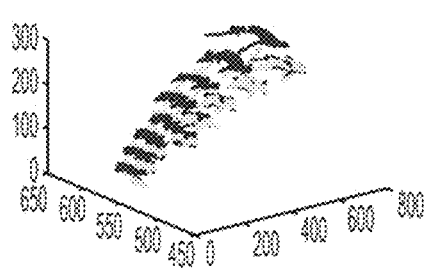
FIG. 8(c) shows the plot in 3D (x-y-t) view, only using the detected temporarily stable features (edge pixels)
Figure 8D:
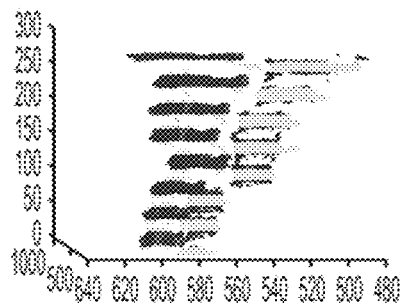
FIG. 8(d) is a view from different angle, which shows the separation of each step clearly.

In one embodiment, the segmentation method can be described as follows. For a frame at t, let $F_{all}(x,y;t)$ denote all detected features on this frame, and $F_{stable}(x,y;t)$ denote the detected temporarily stable features at frame t that has been accumulated from t−3 to t. For the frontal view, assign the detected temporarily stable features to a binary class label using the following rule: 0, if the center of $F_{stable}(x,y;t)$ is on the left (or right) of the center of $F_{all}(x,y;t)$; 1, if else. As shown in FIG. 7, all detected features (edge pixels in the experiment) at a time are illustrated and the green highlighted pixels are the detected temporarily stable edge pixels at that time. It can be easily determined from the data which leg is the supporting leg; hence the step or stride duration or length of a walking cycle can be determined too, as shown in FIGS. 8(a)-(d). FIG. 8(a) shows the x-t view of each detected step and 8(b) shows the y-t view of each detected step when a human walks through a hallway. All detected features (edge pixels) are colored to indicate the step changes, which alternates between left and right legs or feet. FIG. 8(c) shows the plot in 3D (x-y-t) view only using the detected temporarily stable features (edge pixels). FIG. 8(d) is a view from a different angle, which shows the separation of each step clearly.

In general, steps/step changes can be detected from $F_{stable}(x,y;t)$ for a walking sequence from any view angle. FIGS. 9(a) and 9(b) show the center changes of $F_{stable}(x,y;t)$ where (a) shows the XY view of the centers of $F_{stable}(x,y;t)$ and (b) shows its x-t-view. For sagittal views, YT signals might be more useful. For oblique views, both XT and YT should be considered. The signals can be further enhanced or processed to segment each step. Other parameters other than centers of $F_{stable}(x,y;t)$ can also be used.

From the segmented gait cycles, a set of metrics can be estimated in step 60, such as stride duration, cadence, stride length and gait base, etc. Such metrics have been clinically demonstrated to be significant among other movements for analyzing various diseases or injuries. The estimated set of metrics along with other features can then be employed for abnormal gait quantification depending on the application.

Experimental Results

To simulate different types of abnormalities and test how well the selected features differentiate between them, experiments were performed where subjects walk with various ankle weights. The subjects walk back and forth in a hallway where two cameras are mounted at the front and end. Each subject wears an ankle weight of 2.5 and 7.5 lb. in each sequence. Finally, a sequence of normal gait for each subject where no ankle weight is worn is recorded.

Table 1 and 2 below show the step durations of two subjects wearing different amounts of weight on the left ankle. The changes in step (stride) duration by increasing the weights can be seen. For Subject2, the weight affects the step duration of each leg differently. The results match the intuition as Subject1 is taller, heavier and walks faster than Subject2. The cadence of each subject can be easily calculated: for Subject1 the average cadence is 129.68 steps/min without weight; for Subject2, the average cadence is 115.38 steps/min. Both subjects' data shows that the proposed method is sensitive and accurate enough to detect the small changes in step duration.

TABLE 1

Step durations of subject 1 wearing different weights.

| Subject1 No | Step duration in frames | | | | | | | | | avg |
|---|---|---|---|---|---|---|---|---|---|---|
| weight | 13 | 15 | 14 | 14 | 14 | 14 | 13 | 14 | | 13.88 |
| 2.5 lb | 15 | 16 | 15 | 16 | 15 | 16 | 14 | 15 | | 15.25 |
| 7.5 lb | 15 | 15 | 16 | 14 | 16 | 16 | 16 | 16 | 17 | 14 | 15.5 |

TABLE 2

Step durations of subject 2 wearing different weights.

| Subject2 No | Step duration in frames | | | | | | | | | | | avg |
|---|---|---|---|---|---|---|---|---|---|---|---|---|
| weight | 13 | 19 | 10 | 21 | 10 | 21 | 12 | 18 | 10 | 22 | | 15.6 |
| 2.5 lb | 15 | 19 | 11 | 20 | 12 | 20 | 13 | 20 | 15 | 18 | | 16.3 |
| 7.5 lb | 17 | 17 | 17 | 18 | 16 | 20 | 17 | 18 | 18 | 16 | 20 | 18 | 17.67 |

It should be appreciated that aspects of the present disclosure are directed to an efficient and accurate method to segment each step, stride or walking cycle for analyzing gait duration or length. The assessment of gait can be carried out in a wide range of manners according to the requirements of different applications. As such, it should be understood that the system and method set forth above can be used for a range of other purposes.

It should now be understood that the present disclosure provides at least one or more of the following advantages:

Robust to the performance of feature detection (can handle missing features, noise features, etc.)

View independent (can deal with most camera view angles, frontal, sagittal, oblique, etc., (Note: top down view is not generally a good angle for any gait analysis methods)

Computationally efficient (the method is very fast, can be used in real time systems)

Accurate/sensitive (the method is able to detect small changes accurately)

Non-intrusive, with no need to place any device or markers on the subject during the experiments.

Capable of implementation using a low-cost camera with no expensive setups and/or expertise in operating the software.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A computer-implemented method for gait analysis of a subject comprising:
obtaining visual data from an image capture device, the visual data comprising a plurality of image frames of the subject over a period of time walking, the plurality of image frames capturing at least one gait cycle of the gait of the subject, the image capture device including a camera mounted in an elongate hallway in which the subject can walk towards and away from the camera, said visual data including a frontal view of the subject approaching the camera;
detecting one or more prescribed features within the plurality of image frames;
analyzing each of the plurality of image frames to detect cross-frame stability of the one or more prescribed features;
and segmenting the gait of the subject into at least one gait cycle based at least in part on the detected cross-frame stability of the one or more prescribed features.

2. The computer-implemented method for gait analysis of a subject as set forth in claim 1, wherein the one or more prescribed features includes edge/contour/silhouette pixels, Harris corners, dense SIFT/SURF features, color features or other local/regional image features.

3. The computer-implemented method for gait analysis of a subject as set forth in claim 2, further comprising detecting a plurality of spatiotemporal clusters of edge pixels, the spatiotemporal clusters corresponding to temporarily stable features in the plurality of image frames.

4. The computer-implemented method for gait analysis of a subject as set forth in claim 3, further comprising analyzing the plurality of spatiotemporal clusters to segment the gait.

5. The computer-implemented method for gait analysis of a subject as set forth in claim 3, wherein temporarily stable features are features detected to be stationary in more than two image frames and less than 13 image frames.

6. The computer-implemented method for gait analysis of a subject as set forth in claim 1, further comprising analyzing the gait segment for at least one of a stride duration, cadence, stride length or base gait.

7. A system for gait analysis of a subject comprising:
an image capture device operatively coupled to a data processing device, the image capture device configured to capture visual data comprising a plurality of image frames of the subject walking, the plurality of image frames capturing at least one gait cycle of the gait of the subject from a single frontal point of view;
a processor-usable medium embodying computer code, said processor-usable medium being coupled to said data processing device, said computer code comprising instructions executable by said data processing device for view independent gait analysis of the image frames, the instructions configured for:
detecting one or more prescribed features within the plurality of image frames;
analyzing each of the plurality of image frames to detect cross-frame stability of the one or more prescribed features;
and segmenting the gait of the subject into at least one gait cycle based at least in part on the detected cross-frame stability of the one or more prescribed features.

8. The system set forth in claim 7, wherein the one or more prescribed features includes edge/contour/silhouette pixels, Harris corners, dense SIFT/SURF features, color features or other local/regional image features.

9. The system set forth in claim 8, wherein the data processing device is further configured for detecting a plurality of spatiotemporal clusters of edge pixels, the spatiotemporal clusters corresponding to temporarily stable features in the plurality of image frames.

10. The system set forth in claim 9, wherein the data processing device is further configured for analyzing the plurality of spatiotemporal clusters to segment the gait.

11. The system set forth in claim 9, wherein temporarily stable features are features detected to be stationary in more than two image frames and less than 13 image frames.

12. The system set forth in claim 7, wherein the data processing device is further configured for analyzing the gait segment for at least one of a stride duration, cadence, stride length or gait base.

13. The system set forth in claim 7, wherein the obtaining visual data from an image capture device includes using a camera mounted in an elongate hallway in which the subject can walk towards and away from the camera.

14. A non-transitory computer-usable medium for gait analysis of a subject, said computer-usable medium embodying a computer program code, said computer program code comprising computer executable instructions configured for:
- obtaining visual data from an image capture device, the visual data comprising a plurality of image frames of the subject over a period of time walking, the plurality of image frames capturing at least one gait cycle of the gait of the subject, the image capture device including a camera mounted in an elongate hallway in which the subject can walk towards and away from the camera, said visual data including a frontal view of the subject approaching the camera;
- detecting one or more prescribed features within the plurality of image frames;
- analyzing each of the plurality of image frames to detect cross-frame stability of the one or more prescribed features;
- and segmenting the gait of the subject into at least one gait cycle based at least in part on the detected cross-frame stability of the one or more prescribed features.

15. The non-transitory computer-usable medium of claim 14, wherein the one or more prescribed features includes edge pixels.

16. The non-transitory computer-usable medium of claim 15, wherein the computer executable instructions are further configured for detecting a plurality of spatiotemporal clusters of edge pixels, the spatiotemporal clusters corresponding to temporarily stable features in the plurality of image frames.

17. The non-transitory computer-usable medium of claim 16, wherein the computer executable instructions are further configured for analyzing the plurality of spatiotemporal clusters to segment the gait.

18. The non-transitory computer-usable medium of claim 16, wherein temporarily stable features are features detected to be stationary in more than two image frames and less than 13 image frames.

19. The non-transitory computer-usable medium of claim 14, wherein the computer executable instructions are further configured for analyzing the gait segment for at least one of a stride duration, cadence, stride length or gait base.

* * * * *